United States Patent
Evanko et al.

(10) Patent No.: US 10,076,774 B1
(45) Date of Patent: Sep. 18, 2018

(54) COLORMETRIC CLEANER FOR HUMMINGBIRD FEEDERS

(71) Applicant: Hummeze, LLC, Peralta, NM (US)

(72) Inventors: Rebecca Evanko, Peralta, NM (US); Mark Evanko, Peralta, NM (US)

(*) Notice: Subject to any disclaimer, the term of this patent is extended or adjusted under 35 U.S.C. 154(b) by 2 days.

(21) Appl. No.: 15/491,763

(22) Filed: Apr. 19, 2017

Related U.S. Application Data

(60) Provisional application No. 62/329,459, filed on Apr. 29, 2016.

(51) Int. Cl.
| | |
|---|---|
| *B08B 3/08* | (2006.01) |
| *A01N 59/00* | (2006.01) |
| *A01N 25/12* | (2006.01) |
| *C11D 3/48* | (2006.01) |
| *C11D 3/00* | (2006.01) |
| *C11D 3/40* | (2006.01) |
| *C11D 17/00* | (2006.01) |
| *C11D 3/39* | (2006.01) |
| *C11D 3/10* | (2006.01) |
| *C11D 7/12* | (2006.01) |
| *C11D 3/395* | (2006.01) |
| *C11D 3/42* | (2006.01) |

(52) U.S. Cl.
CPC ............. *B08B 3/08* (2013.01); *A01N 25/12* (2013.01); *A01N 59/00* (2013.01); *C11D 3/0047* (2013.01); *C11D 3/40* (2013.01); *C11D 3/48* (2013.01); *C11D 3/10* (2013.01); *C11D 3/39* (2013.01); *C11D 3/3902* (2013.01); *C11D 3/3942* (2013.01); *C11D 3/3953* (2013.01); *C11D 3/42* (2013.01); *C11D 7/12* (2013.01); *C11D 17/003* (2013.01)

(58) Field of Classification Search
CPC ....... C11D 3/0047; C11D 3/39; C11D 3/3902; C11D 3/40; C11D 3/48; C11D 3/3942; C11D 3/3953; C11D 3/42; C11D 3/10; C11D 17/003; C11D 7/12; B08B 3/08; A01N 59/00; A01N 25/12
See application file for complete search history.

(56) References Cited

U.S. PATENT DOCUMENTS

| | | | |
|---|---|---|---|
| 3,913,527 A * | 10/1975 | Kilham ................ | A01K 39/014 119/74 |
| 4,558,662 A | 12/1985 | Peterson | |
| 4,901,673 A | 2/1990 | Overstreet | |
| 4,938,168 A | 7/1990 | Meidell | |
| 5,062,390 A | 11/1991 | Bescherer | |
| 5,269,258 A | 12/1993 | Brown | |
| 5,454,348 A | 10/1995 | Colwell | |

(Continued)

OTHER PUBLICATIONS

"How to Clean a Hummingbird Feeder", WikiHow.com; pp. 1-4; Jul. 12, 2018 (Year: 2018).*

(Continued)

*Primary Examiner* — Sharidan Carrillo
(74) *Attorney, Agent, or Firm* — Nathaniel A. Gilder; Jensen & Puntigam, PS

(57) ABSTRACT

A colorimetric birdfeeder cleaner may comprise a cleansing/disinfecting agent, a pH buffering agent, and a colorant. A hummingbird feeder may be immersed in a colorimetric cleaning solution produced with the colorimetric birdfeeder cleaner, and a change in color of the colorimetric cleaning solution indicates a cleaning process is complete.

8 Claims, 2 Drawing Sheets

(56) References Cited

U.S. PATENT DOCUMENTS

| | | | |
|---|---|---|---|
| 5,507,249 | A | 4/1996 | Shaw |
| 6,834,616 | B2 | 12/2004 | Fort, II |
| 6,932,023 | B1 | 8/2005 | Nauert |
| 7,040,251 | B2 | 5/2006 | Fort, II |
| 7,093,562 | B2 | 8/2006 | Smothers |
| 7,234,418 | B2 | 6/2007 | Fort, II |
| 7,275,500 | B2 | 10/2007 | Fort, II |
| 9,192,148 | B1 | 11/2015 | Hill |
| 2010/0192866 | A1 | 8/2010 | McMullen |
| 2011/0239949 | A1 | 10/2011 | Abbott |
| 2012/0006272 | A1* | 1/2012 | Colvin ................. A01K 39/012 119/51.01 |

OTHER PUBLICATIONS

Chambers, "Hummingbird Feeders," Internet Article, http://www.hummingbirds.net/feeders.html, accessed Apr. 12, 2017.
Mason, "Loving Hummingbirds to Death," Internet Article, http://www.almostdailynews.com/2012/06/080/hummingbirds-dont-love-them-to-death/ , Jun. 8, 2012.
Surfbirds, "How to Clean Hummingbird Feeders," Internet Article, http://www.surfbirds.com/bird-feeders/clean_hummingbird_feeders.html, accessed Apr. 12, 2017.
Williamson, "Keeping Hummingbird Feeders Clean," Internet Article, https://fieldguidetohummingbirds.wordpress.com/2014/09/01/keeping-hummingbird-feeders-clean/, Sep. 1, 2014.

* cited by examiner

COLORMETRIC CLEANER FOR HUMMINGBIRD FEEDERS

CROSS REFERENCE TO RELATED APPLICATIONS

This non-provisional patent application claims priority of U.S. Provisional Patent Application Ser. No. 62/329,459, filed Apr. 29, 2016, and entitled "Colormetric Cleaner for Hummingbird Feeders", which is incorporated by reference herein.

BACKGROUND

The feeding of hummingbirds brings many people much happiness and pleasure. These birds provide a delightful connection between humans and nature, permitting a closer look and participation in the beauty of the natural world.

Providing feeding solution for hummingbirds is very simple: a mixture of sugar and water that approximates the flower nectar on which these birds naturally feed. Unfortunately, however, the sugary liquid and the outside placement of the feeders in which the liquid is placed combine to form a potent circumstance for the cultivation of bacteria and black mold.

Tragically, black mold is highly toxic to hummingbirds. To overcome the risk to these birds, proper cleaning of the feeders is critical. There are several methods of feeder cleaning that are predominantly used, often involving harsh or heavily odiferous agents such as bleach or vinegar, and frequently—if not always—involving the time-consuming process of scrubbing or brushing the small orifices and reservoirs of the feeders in order to eliminate mold and bacteria.

Common configurations of hummingbird feeders are disclosed in U.S. Pat. No. 7,275,500 (Fort et. al.), U.S. Pat. No. 7,234,418 (Fort et. al.), U.S. Pat. No. 7,040,251 (Fort et. al.), U.S. Pat. No. 6,834,616 (Fort et. al.), U.S. Pat. No. 7,093,562 (Smothers), U.S. Pat. No. 5,507,249 (Shaw), U.S. Pat. No. 5,269,258 (Brown), U.S. Pat. No. 4,938,168 (Meidell), U.S. Pat. No. 4,901,673 (Overstreet), and U.S. Pat. No. 4,558,662 (Peterson). The typical hummingbird feeder primarily comprises a transparent, cylindrical reservoir usually made of glass or polycarbonate plastic to hold a sugar-solution liquid favored by hummingbirds as a source of fluid energy.

The feeder is often suspended by a hook and hanger attachment to various substrates, such as branches of trees, or rain gutters or fascia boards on houses, in order to permit the birds free access and flight path to and from the apparatus. The hook is frequently attached to a plastic cap or covering that is affixed, usually through a screw-on system, to the reservoir. Feeders are often red in color and contain red and yellow components, as these shades are known to attract hummingbirds.

The base of the feeder often comprises a variant on a closed, cylindrical bowl configuration as a means to provide a platform with small apertures through which the liquid can be extracted by the elongated beaks of the hummingbirds. While the design forms of these "feeding holes" can take different shapes, including replicating the petals or stamens of flowers, the principle is constant: it is a small opening or series of small openings through which the sugary liquid can be extracted by the hummingbird.

Because of the combination of small apertures and sugary liquid, a concomitant problem with hummingbird feeders is the potential for rapid mold and bacterial growth, especially in places that are difficult to adequately clean. Regular cleaning is imperative to the health of hummingbirds, and typical methods to achieve this involve, variously, using bleach, vinegar, hot water and soap, or rice. These solutions, with varying degrees of environmental safety, still require the need to vigorously brush or scrub the feeder parts, especially the reservoir and feeding holes in which mold can stubbornly lurk.

Approaches to cleaning the feeders differ widely; however, there is agreement that the presence of mold and bacteria can be deadly to hummingbirds. The following are quotes from various sources regarding hummingbird feeder cleaning:

"At least once a month, clean the feeder thoroughly with a solution of ¼ cup bleach to one gallon of water. Soak the feeder in this solution for one hour, then clean with a bottle brush. Rinse well with running water" (Lanny Chambers, "Hummingbird Feeders," Internet Article, June 2007).

"It's important to keep the dreaded black mold off your Hummingbird Feeders. Dirty feeders can cause illness and death in hummingbirds . . . . Fill the bottle up with 2 parts water to 1-part vinegar and let it soak for several hours . . . [and] use a stiff brush to clean the base and also a bottle brush for the bottle" (SurfBirds, "How to Clean Hummingbird Feeders," Internet Article, accessed Apr. 12, 2107).

"Use a Bottle/Thermos Brush or a Hummingbird Feeder Brush and scrub inside of the hummingbird feeder tank really well, working to get out any goop and gunk that might have grown inside. This needs to be done even if you don't see anything inside the tank as mold may just be starting to grow and may not yet be visible. Make sure to scrub the base and flowers with soap and water as well because goop can sometimes clog these components" (World of Hummingbirds, "Cleaning a Hummingbird Feeder," Internet Article, accessed Apr. 12, 2017).

"A 15-minute soak in a dilute solution of chlorine bleach (1-part bleach in 10 or more parts water) is very effective at killing black mold on non-porous surfaces, but an hour-long soak in white vinegar is a less toxic alternative . . . . In either case, follow up on the soak with a thorough brushing to remove dead mold colonies and other organic growths, then rinse well and let the feeder dry before refilling to allow the odor to dissipate" (Sheri L. Williamson, "Keeping Hummingbird Feeders Clean," Internet Article, Sep. 1, 2014).

"An even safer mold killer that's much kinder to your nose than bleach or vinegar is 3% hydrogen peroxide, the medicinal kind you can buy in any drug or grocery store . . . . Follow the treatment with a good scrub, including the ports, and rinse well to remove any debris" (Sheri L. Williamson, "Keeping Hummingbird Feeders Clean," Internet Article, Sep. 1, 2014.).

"Hummingbird feeders must be kept clean and free from mold and fungus, or the tiny hum-buzzers you so enjoy could develop a serious and deadly fungus infection. This infection causes the tongue to swell, making it impossible for the bird to feed. Starvation is a slow and painful death. The proper care of hummingbird feeders requires a significant commitment of time and energy" (Kimberly Mason, "Loving Hummingbirds to Death," Internet Article, Jun. 8, 2012).

United States Patent Publication No. 2011/0239949 (Abbott) accedes the "risk of internal injury to hummingbirds resulting from ingestion of spoiled liquid sugar solution or other food . . . resulting in [the possibility of] intestinal or other internal damage," the resulting conjecture that this is much more likely to occur in hummingbird feeders with large holding capacities as opposed to smaller capacity is incorrect in relation to an inalienable fact: anytime a sugary substance comes into contact with mold spores or bacterium—often through the bird's beak itself—in combination with heat and moisture, the risk of mold growth is significant. And, where there is mold and bacteria, there is the need for sufficient cleaning.

It is acknowledged that the size of the reservoir and component parts make access to the interior of the feeders easier—such as having a wider opening to the reservoir that will more easily accommodate a cleaning brush—a point made in U.S. Pat. No. 5,454,348 (Colwell et al.), which describes a typical hummingbird feeder as containing a cleaning opening "of sufficient size for enabling the cleaning of the reservoir." However, the small apertures required in feeders, into which the hummingbirds penetrate their beaks, simulating the action of extracting nectar from a flower's stamens, is conducive to cultivating mold and the size of the reservoir and parts neither eliminate nor mitigate that reality. Moreover, the problem of cleaning a hummingbird feeder is not just a matter of the size of openings for access; rather, it is the need for scrubbing, brushing, or otherwise investing considerable time and energy in sufficiently cleaning these devices.

While U.S. Pat. No. 9,192,148 (Hill) exhorts the need for a more sterile form of nectar liquid for the feeders as a means to protect hummingbirds from the growth of mold and bacteria, Hill acknowledges the need to still replace the nectar and, moreover, that this task is "typically cumbersome and time-consuming for the user, often requiring additional cleaning of the hummingbird feeder."

Hill further points out that it is "generally known that hummingbirds . . . are creatures of habit, returning to a feeder that previously had a fresh nectar supply . . . . Stale nectar may make a hummingbird sick. Insects may be attracted to fresh or spoiling nectar, which may exacerbate or accelerate spoilage and bring further risks to the health of hummingbirds." Such observations underscore the importance of finding a safe, easy, time-efficient, and effective means of cleaning hummingbird feeders.

Problems in cleaning the feeders is evident in United States Patent Publication No. 2010/0192866 (McMullen), which acknowledges that a "critical problem exists when the nectar spoils[,] resulting in the health of hummingbirds being endangered." Moreover, "[t]he feeding solution spoils and becomes contaminated within a relatively short period of time. Spoilage results in the accumulation of mold slime and . . . [p]hysical changes . . . such as changes in acid pH content, specific gravity, presence of alcohol, [and] presence of bacteria." These elements also yield potential health risks for humans.

Frequent cleaning of the hummingbird feeders is crucial to minimize or, preferably, eliminate the growth of mold and bacteria. The nature of the time involved in cleaning the feeders is especially recognized in U.S. Pat. No. 6,932,023 (Nauert) as well as McMullen. Adequate cleaning, as McMullen recognizes, is a multi-step process and is difficult for several reasons, including the need for a "variety of brushes to clean the interior parts" as the "feeding apertures are very small to accommodate the beak of a hummingbird, having an opening of about one-eighth of an inch." McMullen further describes the process of cleaning hummingbird feeders as a "time consuming, messy, and unsanitary process that detracts from the feeding of hummingbirds."

Although McMullen proposes a disposable hummingbird feeder as a means to counter the problem with mold and bacteria growth, the use of disposable products as opposed to maintenance of more permanent hummingbird feeders is questionable in terms of environmental responsibility and sustainability. Even in light of McMullen's claim of using "an economical feeder design using biodegradable or recyclable materials," the fact of the feeder being discarded after use is neither particularly economical, nor environmentally sustainable. Many hummingbird enthusiasts, by way of their interest in the natural world and its creatures, are also concerned about the natural environment and are reluctant to participate in such a "throwaway" mentality. This does not, therefore, resolve the problem of the need for a safe, time-efficient, easy, effective, and environmentally-sensitive means of cleaning the feeders.

McMullen accedes that prior art relating to hummingbird feeders is "relatively crowded," and yet it can indeed be appreciated "that there is a continuing interest in providing improvements to such hummingbird feeders." There has not, however, been a concomitant approach to improving the means of cleaning the feeders.

As stated in U.S. Pat. No. 5,062,390 (Bescherer et al.), "the hummingbird, because of its high rate of metabolism, requires large amounts of this food [nectar or nectar substitute]." This necessitates the provision of a constant, clean supply. And yet, as noted in the patent, hummingbird feeders have "suffered from the defect that they have been difficult (if not impossible) to clean" and that "if the nectar is not removed and the container completely cleaned, the danger arises that the nectar can ferment and generate chemicals or bacteria that are harmful to the hummingbird, particularly to the liver of the bird." These observations make not only the need for an effective, safe, and time-saving method of cleaning feeders apparent, but also highlight the lack of such an invention to date.

In summary, there is a need in the industry for a simple, safe, effective, easy-to-use, environmentally-responsible, and time-saving method for cleaning hummingbird feeders.

SUMMARY

Colorimetric cleaners, such as may be used to clean hummingbird feeders, and corresponding methods of use are disclosed. In some examples, a colorimetric cleaner may comprise a concentrated colorimetric cleaning powder composition. The concentrated colorimetric cleaning powder composition may comprise, inter alia, a cleansing/disinfecting agent such as sodium percarbonate; a pH buffering agent such as sodium bicarbonate; and a colorant, such as an edible colorant gel formulation. Example methods of using such a concentrated colorimetric cleaning powder composition may include mixing the concentrated colorimetric cleaning powder composition with water; immersing at least a portion of a hummingbird feeder in the water mixed with the concentrated colorimetric cleaning powder composition; and waiting for a change in color of the water mixed with the concentrated colorimetric cleaning powder composition. Additional aspects of this disclosure are described in further detail below.

BRIEF DESCRIPTION OF THE DRAWINGS

Various features and attendant advantages of the disclosed technologies will become fully appreciated when considered in conjunction with the accompanying drawings, in which like reference characters designate the same or similar parts throughout the several views, and wherein.

DETAILED DESCRIPTION OF THE INVENTION

Figure 1:
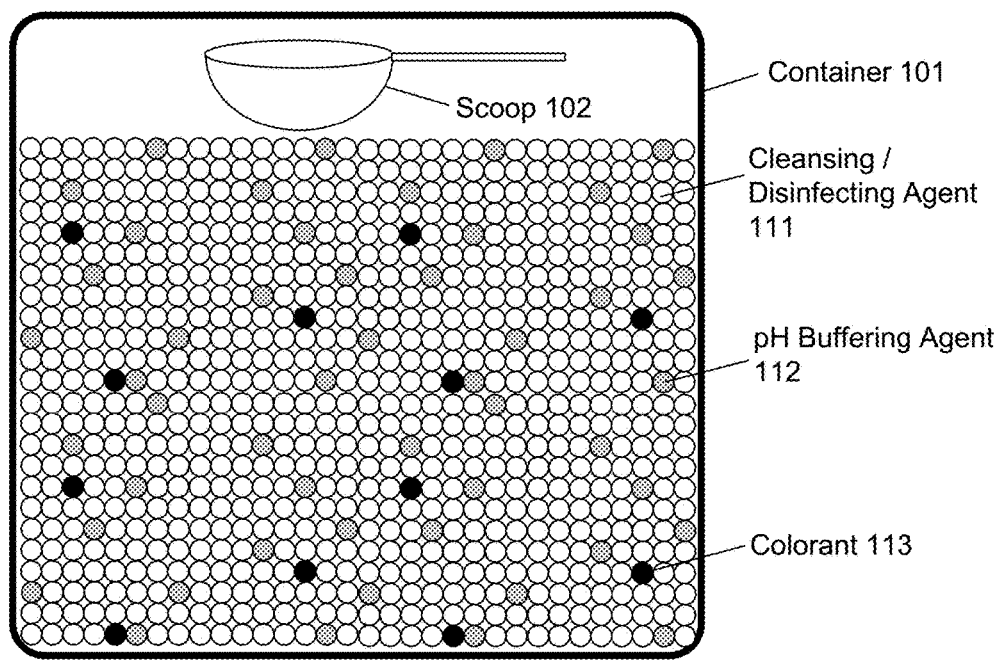
FIG. 1 illustrates an example concentrated colorimetric birdfeeder cleaner composition.

Prior to explaining embodiments of the invention in detail, it is to be understood that this disclosure is not limited to the details of construction or arrangements of the components and method steps set forth in the following description or illustrated in the drawings. Embodiments of this disclosure are capable of other embodiments and of being practiced and carried out in various ways. Also, it is to be understood that the phraseology and terminology employed herein are for the purpose of the description and should not be regarded as limiting.

This disclosure generally provides colorimetric birdfeeder cleaners, such as may be used to clean hummingbird feeders in particular, and corresponding methods of use. The term "colorimetric" as used herein refers to changing color, which may be used to indicate a length of time, a cleaning state, or both. Colorimetric birdfeeder cleaners may generally comprise a cleansing/disinfecting agent, a pH buffering agent, and a colorant, as described in further detail below.

FIG. 1 illustrates a concentrated colorimetric cleaning powder composition, which may provide a colorimetric birdfeeder cleaner in accordance with at least some embodiments of the present disclosure. The concentrated colorimetric cleaning powder composition (also referred to herein as the "concentrated composition") comprises a cleansing/disinfecting agent 111, a pH buffering agent 112, and a colorant 113. The concentrated composition is illustrated inside a container 101 along with a scoop 102, which may be used to measure an amount of the concentrated composition for use thereof. The concentrated composition may be mixed with liquid, such as water, in order to produce a colorimetric cleaning solution, as described herein.

In some embodiments, the cleansing/disinfecting agent 111 may comprise sodium percarbonate powder. The pH buffering agent 112 may comprise sodium bicarbonate powder. And the colorant 113 may comprise an edible colorant gel formulation. Other cleansing/disinfecting agents, pH buffering agents, and/or colorants may be used in some embodiments, and embodiments of this disclosure need not necessarily be limited to sodium percarbonate, sodium bicarbonate, or edible colorant gel formulations. For example, in some embodiments, the cleansing/disinfecting agent 111 and/or pH buffering agent 112 may comprise chemicals/substances from the peroxides, chlorates, and perchlorates family of chemicals. The colorant 113 may comprise any food coloring agent and/or a natural source of colorant such as, for example, cinnamon, which would add a brownish, burnt-orange red color.

The concentrated composition illustrated in FIG. 1 is generally in powder form, however, the size of the powder particles may vary from fine/small to coarse/large, depending on the desired properties of the composition. Also, when colorant 113 is an edible colorant gel formulation, gel particles of any desired sizes may be mixed with powder cleansing/disinfecting agent 111 and powder pH buffering agent 112. Furthermore, in some embodiments, the concentrated composition may take other forms, e.g., the cleansing/disinfecting agent 111, pH buffering agents 112, and colorant 113 may be mixed in a concentrated liquid solution. At the time of use, the concentrated liquid solution may be further mixed with liquid, such as water, in order to produce the colorimetric cleaning solution described herein.

The term "concentrated" as used herein refers to compositions or solutions having higher strength than necessary for birdfeeder cleaning applications, and which therefore are preferably diluted with water or other diluting agents prior to use. While the concentrated composition illustrated in FIG. 1 is referred to as concentrated, this disclosure is not limited to "concentrated" compositions. Furthermore, concentrated compositions according to this disclosure may have a variety of different concentration levels, as will be appreciated.

Figure 2:
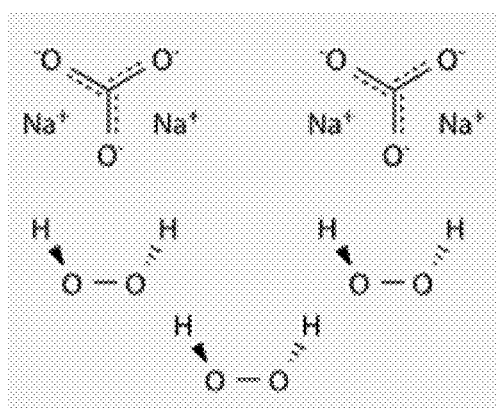
FIG. 2 illustrates an example molecular structure for sodium percarbonate, such as may be included in colorimetric birdfeeder cleaner compositions described herein.

An example sodium percarbonate cleansing/disinfecting agent 111 may comprise $C_2H_6Na_4O_{12}$, e.g., in a form such as illustrated in FIG. 2, or its chemical equivalents. Sodium percarbonate oxidizes, cleans, and disinfects. Sodium percarbonate also quickly dissolves in water and separates into sodium carbonate (soda ash) and hydrogen peroxide. Neither hydrogen peroxide nor sodium carbonate will find its way to aquatic ecosystems, as waste water treatment plants will degrade the first and neutralize the second into non-toxic bicarbonate. Sodium has low toxicity, and the breakdown of sodium percarbonate to sodium is too low to negatively affect aquatic life. Based on available research data, the use of sodium percarbonate in household cleaning products has no adverse effect on the aquatic organisms of the receiving water. Regarding the effect of sodium percarbonate on human health, while local skin and eye irritation on contact is possible, sodium percarbonate in solutions such as described herein are generally too low to cause skin irritation.

Figure 3:
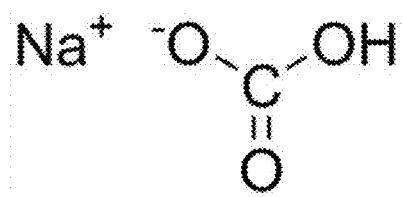
FIG. 3 illustrates an example molecular structure for sodium bicarbonate, such as may be included in colorimetric birdfeeder cleaner compositions described herein.

An example sodium bicarbonate pH buffering agent 112 may comprise $CHNaO_3$, e.g., in a form such as illustrated in FIG. 3, or its chemical equivalents. The inclusion of a pH buffering agent 112 such as sodium bicarbonate reduces the acidity of the sodium percarbonate cleansing/disinfecting agent 111. Furthermore, a sodium bicarbonate pH buffering agent 112 may create an alkalizing effect for colorimetric cleaning solutions produced with the concentrated composition, thereby yielding colorimetric cleaning solutions that are gentler for the plastic and metallic components of the typical hummingbird feeders. Sodium bicarbonate also has fungicidal properties that are effective in eliminating the mold that can grow so quickly and prolifically on the hummingbird feeders as a result of the sugar-solution used for hummingbirds.

Example edible colorant gel formulation colorants 113 may activate colorimetric components of colorimetric cleaning solutions made with concentrated compositions such as illustrated in FIG. 1, in order to indicate completion of cleaning processes. As a gel-based product, the edible colorant gel formulation colorant 113 remains stable and does not activate the transition of sodium percarbonate into hydrogen peroxide and sodium carbonate, as a liquid-based colorant might. Further, the gel colorant is food-grade, edible, and non-toxic. Its components may include a colorant such as erythrosine (E127), cochineal or carminic acid (E120), indigo carmine (E132), brilliant blue FCF (E133), copper complexes of chlorophylls and chlorophyllins (E141), annatto, bixin, or norbixin (E160b), paprika oleoresin, capsanthin, or capsorubin (E160c), lycopene (E160d), canthaxanthin (E161g), beetroot red or betanin (E162), curcumin (E100), riboflavin (E101), or tartrazine (E102).

Additional components of edible colorant gel formulation colorant 113 include, but are not limited to: water; high fructose corn syrup; glycerin; sugar; modified food starch; carrageenan gum; sodium benzoate; potassium sorbate; xanthan gum; or citric acid.

The inclusion of colorant 113 in the concentrated composition illustrated in FIG. 1 yields a concentrated composition which, when mixed with water, will gradually alter the shade of the resulting colorimetric cleaning solution from colored, when a cleaning process is initiated, to substantially clear or lightly colored, after the cleaning process is complete. This color change provides a simple, effective, and time-saving method for cleaning hummingbird feeders. It is simple in that the consumer need not time the cleaning process, nor actively participate in it. The consumer need not mix ingredients or weigh and measure processes other than mixing one or more scoops of the composition into a volume of water.

The concentrated composition illustrated in FIG. 1 may be mixed according to a variety of different ratios. In some embodiments, the concentrated composition may comprise a ratio of about 60 grams (g) sodium percarbonate, to about 1 g sodium bicarbonate, to about 0.1 milliliter (mL) colorant. In some embodiments, the concentrated composition may comprise a ratio of about 60 g sodium percarbonate, to about 1 g-25 g sodium bicarbonate, to about 0.1 mL-0.5 mL colorant.

In some embodiments, the concentrated composition may comprise from 65.87% to 98.24% by weight of the sodium percarbonate, from 1.6% to 33.3% by weight of the sodium bicarbonate, and from 0.16% to 0.83% by weight of the colorant gel formulation. For example, one optional ratio may include 98.24% sodium percarbonate, 1.6% sodium bicarbonate, and 0.16% colorant gel formulation. Further optional ratios may include, e.g., from 66.54% to 98.23% by weight of the sodium percarbonate, or from 65.87% to 66.53% by weight of the sodium percarbonate. Further optional ratios may include, e.g., 1.7% to 33.3% by weight of the sodium bicarbonate. Further optional ratios may include, e.g., from 0.17% and 0.33% by weight of the colorant gel formulation, or from 0.34% to 0.83% by weight of the colorant gel formulation.

The concentrated composition illustrated in FIG. 1 may be mixed in water, according to a variety of different ratios, to produce a colorimetric cleaning solution. For example, in some embodiments, about 1 tablespoon of the concentrated composition may be mixed per 2 gallons of water. Alternatively, in metric terms, about 15 g of the concentrated composition may be mixed per 7.5 liters of water. A hummingbird feeder or other object to be cleaned may be immersed in the resulting colorimetric cleaning solution, and may remain immersed until a color of the colorimetric cleaning solution has changed, e.g., about 30 minutes.

Figure 4:
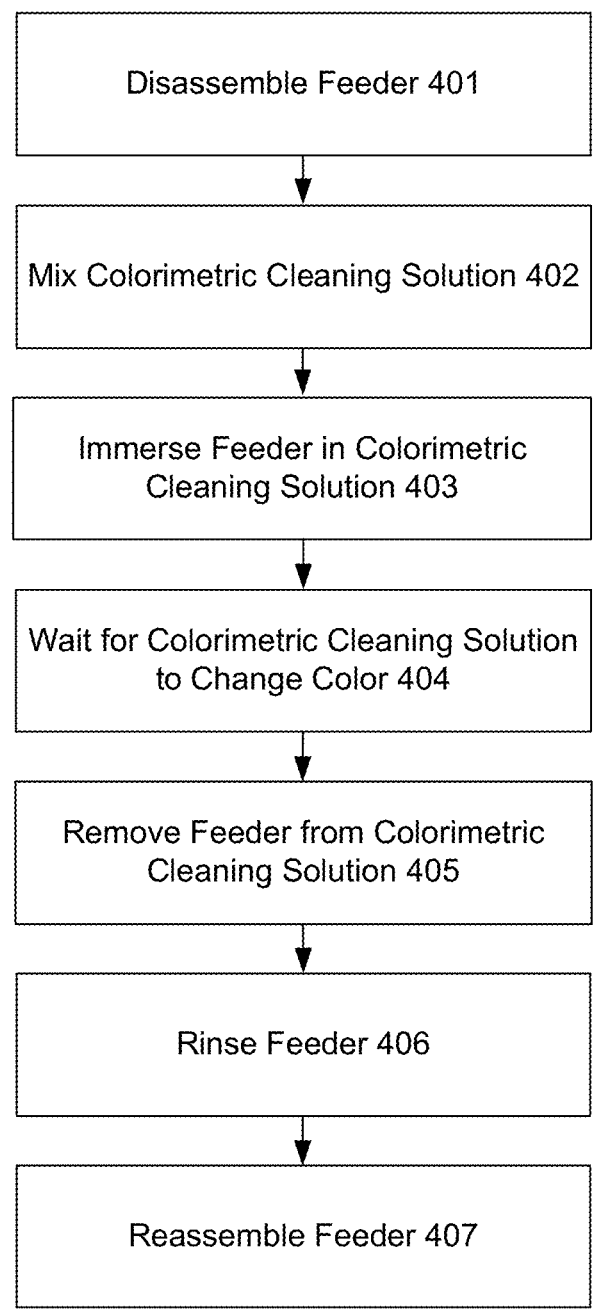
FIG. 4 illustrates an example method to clean hummingbird feeders.

FIG. 4 illustrates an example method to clean hummingbird feeders, in accordance with at least some embodiments of the present disclosure. FIG. 4 includes the example operations of "disassemble feeder" 401, "mix colorimetric cleaning solution" 402, "immerse feeder in colorimetric cleaning solution" 403, "wait for colorimetric cleaning solution to change color" 404, "remove feeder from colorimetric cleaning solution" 405, "rinse feeder" 406, and "reassemble feeder" 407. It will be appreciated that various of the illustrated operations may be omitted, modified, or re-ordered in some embodiments.

At the "disassemble feeder" operation 401, a hummingbird feeder may be disassembled into one or more parts. At the "mix colorimetric cleaning solution" operation 402, in some embodiments, a concentrated composition such as described in connection with FIG. 1 may be mixed with water in order to produce a colorimetric cleaning solution. The ratios described herein may be observed, e.g., about 15 g of concentrated colorimetric cleaning powder composition per 7.5 liters of water. In order to properly dissolve the concentrated composition, warm or hot water may be used, e.g., water having temperature over about 37 degrees Celsius. Mixing may be continued until the powder is substantially dissolved.

At the "immerse feeder in colorimetric cleaning solution" operation 403, at least a portion of the hummingbird feeder to be cleaned may be carefully and completely immersed in the colorimetric cleaning solution produced at operation 402. At the "wait for colorimetric cleaning solution to change color" operation 404, the humming bird feeder or portion thereof may remain immersed while the user waits for an observable change in color of the colorimetric cleaning solution, e.g., about 20-40 minutes. The color change may be, e.g., a change from colored to clear, or a change from relatively dark colored to relatively light colored.

At the "remove feeder from colorimetric cleaning solution" operation 405, after the color change observed at operation 404, the at least a portion of the hummingbird feeder may be removed from the colorimetric cleaning solution. At the "rinse feeder" operation 406, the at least a portion of the hummingbird feeder may be rinsed with water in order to rinse colorimetric cleaning solution off of the feeder. At the "reassemble feeder" operation 407, the at least a portion of the hummingbird feeder may be reassembled with any other portions of the feeder. The feeder is then clean and ready for re-use.

Using colorimetric cleaning solutions described herein, there is no harm to the feeder if they are left suspended in the solution for longer than the time it takes for the colorimetric cleaning solution to change color. There is also no need for brushing or scrubbing. Once the colorimetric cleaning solution color has changed, the feeder may simply be rinsed and reassembled, and it is ready for use again.

Furthermore, the colorimetric cleaning solutions described herein are environmentally responsible, as they need not include harsh chemicals such as bleach to remove the mold that is potentially so dangerous to hummingbirds. There is minimal resulting risk to humans, birds, or other wildlife.

While various embodiments have been disclosed herein, other aspects and embodiments will be apparent to those skilled in art. Therefore, it is intended that claimed subject matter not be limited to the particular examples disclosed, but that such claimed subject matter also may include all implementations falling within the scope of the appended claims, and equivalents thereof.

The invention claimed is:

1. A method to clean hummingbird feeders, comprising the steps of:
    mixing a concentrated colorimetric cleaning powder composition with water in order to produce a colorimetric cleaning solution, the concentrated colorimetric cleaning powder composition comprising:
        a cleansing/disinfecting agent comprising sodium percarbonate;
        a pH balancing agent comprising sodium bicarbonate; and
        an edible colorant gel formation;
    cleaning the hummingbird feeder by immersing at least a portion of the hummingbird feeder in the colorimetric cleaning solution;

detecting completion of said cleaning by monitoring a change in color of the colorimetric cleaning solution; and removing the at least a portion of the hummingbird feeder from the colorimetric cleaning solution.

2. The method to clean hummingbird feeders of claim 1, wherein the concentrated colorimetric cleaning powder composition is from 65.87% to 98.24% by weight of the sodium percarbonate, from 1.6% to 33.3% by weight of the sodium bicarbonate, and from 0.16% to 0.83% by weight of the colorant gel formulation.

3. The method to clean hummingbird feeders of claim 1, further comprising disassembling the hummingbird feeder prior to immersing the at least a portion of the hummingbird feeder.

4. The method to clean hummingbird feeders of claim 1, wherein mixing the concentrated colorimetric cleaning powder composition with water comprises mixing about 15 grams of the concentrated colorimetric cleaning powder composition per 7.5 liters of water.

5. The method to clean hummingbird feeders of claim 1, wherein the water temperature is over 37 degrees Celsius.

6. The method to clean hummingbird feeders of claim 1, wherein mixing the concentrated colorimetric cleaning powder composition with water comprises mixing the colorimetric cleaning powder composition until the powder is dissolved.

7. The method to clean hummingbird feeders of claim 1, further comprising rinsing the at least a portion of the hummingbird feeder with water.

8. The method to clean hummingbird feeders of claim 3, further comprising reassembling the hummingbird feeder after monitoring for the change in color of the colorimetric cleaning solution.

* * * * *